(12) United States Patent
Sheard et al.

(10) Patent No.: US 8,129,191 B2
(45) Date of Patent: Mar. 6, 2012

(54) MONITORING METHOD AND APPARATUS

(75) Inventors: Paul Sheard, Great Doddington (GB); Marika Reay, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 1266 days.

(21) Appl. No.: 11/013,353

(22) Filed: Dec. 17, 2004

(65) Prior Publication Data

US 2005/0137481 A1 Jun. 23, 2005

Related U.S. Application Data

(60) Provisional application No. 60/620,968, filed on Oct. 22, 2004.

(30) Foreign Application Priority Data

Dec. 18, 2003 (GB) .................................. 0329288.5

(51) Int. Cl.
*G01N 33/00* (2006.01)
(52) U.S. Cl. ........................................................ 436/86
(58) Field of Classification Search .............. 422/68.1, 422/58, 81, 95; 436/86, 165, 178, 518
See application file for complete search history.

(56) References Cited

U.S. PATENT DOCUMENTS

| | | | |
|---|---|---|---|
| 5,504,013 A | 4/1996 | Senior | |
| 5,622,871 A | 4/1997 | May et al. | |
| 6,071,294 A | 6/2000 | Simons et al. | |
| 6,117,644 A | 9/2000 | DeBold | |
| 6,235,241 B1 | 5/2001 | Catt et al. | |
| 6,363,772 B1 | 4/2002 | Berry | |
| 6,399,398 B1 | 6/2002 | Cunningham et al. | |
| 6,600,997 B2 | 7/2003 | Deweese et al. | |
| 6,663,833 B1 * | 12/2003 | Stave et al. | 422/81 |
| 7,074,194 B2 | 7/2006 | Crosby et al. | |
| 2002/0019707 A1 * | 2/2002 | Cohen et al. | 702/30 |
| 2002/0060247 A1 | 5/2002 | Krishnaswamy | |
| 2002/0170823 A1 | 11/2002 | Housefield et al. | |
| 2003/0073931 A1 | 4/2003 | Boecker et al. | |
| 2004/0018577 A1 * | 1/2004 | Emerson Campbell et al. | 435/7.93 |
| 2005/0042589 A1 * | 2/2005 | Hatlestad et al. | 434/262 |
| 2005/0148029 A1 * | 7/2005 | Buechler et al. | 435/7.1 |
| 2006/0234304 A1 | 10/2006 | Amann-Zalan et al. | |
| 2008/0221022 A1 * | 9/2008 | Goy et al. | 514/12 |

FOREIGN PATENT DOCUMENTS

EP 1151304 1/2000
(Continued)

OTHER PUBLICATIONS

Apple FS, European Society of Cardiology and American College of Cardiology guidelines for redefinition of myocardial infarction: how to use existing assays clinically and for clinical trials; *Am Heart J.* Dec. 2002;144(6):981-6.

(Continued)

*Primary Examiner* — Jill Warden
*Assistant Examiner* — Dwan A Gerido
(74) *Attorney, Agent, or Firm* — Steptoe & Johnson LLP

(57) ABSTRACT

A device for remote management of patients suffering from heart failure and hypertension can measure one or more biomarker. The device aids in monitoring the efficacy and safety of treatment in such patients.

4 Claims, 1 Drawing Sheet

FOREIGN PATENT DOCUMENTS

| WO | WO 00/28072 | 5/2000 |
|---|---|---|
| WO | WO 02/078533 | 10/2002 |
| WO | WO 02/083913 | 10/2002 |
| WO | WO 03/082091 | 10/2003 |
| WO | WO 2005/027716 | 3/2005 |

OTHER PUBLICATIONS

Braunschweig, F. et al., *The European J. of Heart Failure*, 8(2006), 797-803.
Braunschweig, F; *J Cardiovasc Electrophysiol*. Jan. 2002;13(1 Suppl):S68-72.
Chen YN, *Ann Clin Biochem*. Jul. 1999;36 (Pt 4):433-7.
Erlenkotter A, *Anal Bioanal Chem*. Jan. 2002;372(2):284-92.
Gottlieb SS, et al., *J Card Fail*. Jun. 2002;8(3):136-41.
Horwich, TB; *Circulation*. Aug. 19, 2003;108(7):833-8.
Kawai K; *Am Heart J*. Jun. 2001;141(6):925-32.
Koenig W, et al. *Clin Chem*. 10.1373/clinchem.2004.041889 Nov. 2004.
Kohno M; *Am J Med*. Mar. 1995;98(3):257-65.
Kosiborod, M., et al. *Am. J. Med*. 2003, 114: 112-119.
Kucher, N. et al., *Circulation* 108, No. 18 (2003), 2191-2194.
Kyriakides ZS, et al. *Clin Cardiol* Apr. 2000; 23(4): 285-8.
Latini, *Circulation* Nov. 5, 2002;106(19):2454-8.
Lee,SW; *Am J Kidney Dis*. Jun. 2003;41(6):1257-66.
Leger F, *Eur J Cancer*. Jan. 2002;38(1):52-6.
Li, N. et al., *J. of Zhejiang University Science* 6B, No. 9 (2005), 877-884.
Lindahl, B. et al., *J. American College of Cardiology*, 45 (2005), 533-541.
McKelvie, *Circulation* Sep. 7, 1999;100(10):1056-64.
Murdoch DR; *Am Heart J*. Dec. 1999;138(6 Pt 1):1126-32.
Mussap, M; *Kidney International*, vol. 61 (2001), pp. 1453-1461.
Nakamura T, et al. *J. Am. Coll. Cardiol*. May 15, 2002;39 (10):1657-63.
Newman, DJ, *Ann Clin Biochem*. Mar. 2002;39(Pt 2):89-104.
Perrone RD et al, *Clin Chem*. Oct. 1992;38(10):1933-53.
Robertshaw M, Lai KN, Swaminathan R. *Br J Clin Pharmacol* 1989;28:275-280.
Tombach B, *Clin Chim Acta*. Oct. 2001; 312(1-2):129-34.
Troughton, *Lancet* 2000, 355:1126-30.
Wahab, et al., "Is Blood Glucose an Independent Predictor of Mortality in Acute Myocardial Infarction in the Thrombolytic Era?" (2002) *J. Am. Coll. Cardiol.*, 40: 1748-1754.

* cited by examiner

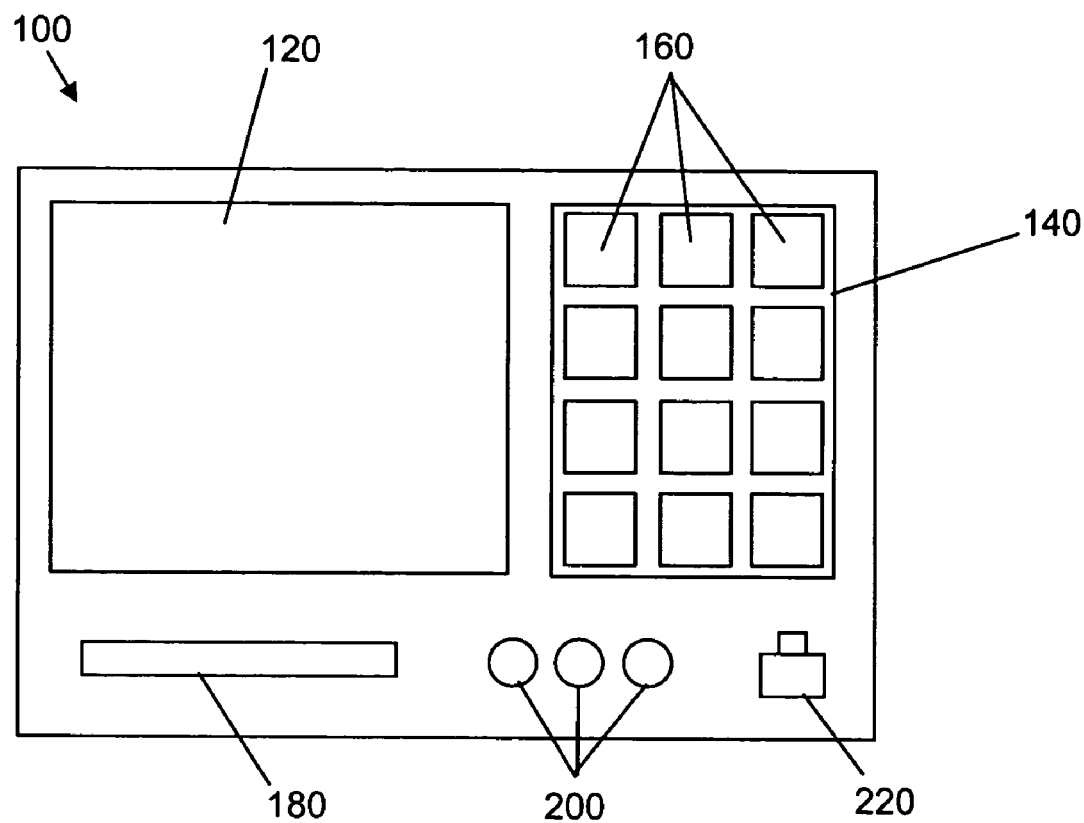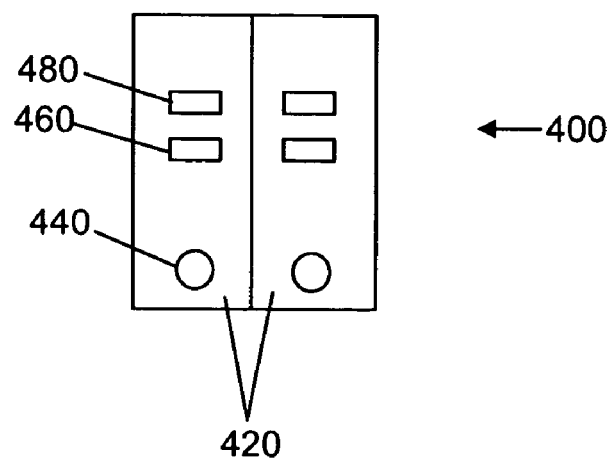

MONITORING METHOD AND APPARATUS

CLAIM OF PRIORITY

This application claims priority to U.S. Patent Application No. 60/620,968, filed on Oct. 22, 2004, and to U.K. provisional application No. 0329288.5, filed Dec. 18, 2003, each of which is incorporated by reference in its entirety.

TECHNICAL FIELD

This invention relates to a method and apparatus for monitoring a patient.

BACKGROUND

Heart failure is a chronic, progressive disease that affects 1.5-2% of the general population of the Western world. The prevalence and incidence of heart failure is growing due to an aging population and a greater number patients who survive a myocardial infarction.

Clinically, heart failure is characterized by a syndrome of breathlessness and fatigue, often accompanied by fluid retention, as indicated by an elevated jugular venous pressure and edema. The progression of heart failure is defined in four stages. The term heart failure refers to all of these.

Stage A—at risk: patients at high-risk of developing heart failure (patients with coronary heart disease, diabetes, hypertension, and/or valvular heart disease).

Stage B—pre-heart failure: patients with structural heart disease but without clinical heart failure symptoms, many of whom have decreased systolic function.

Stage C—heart failure: patients who have prior or current symptomatic heart failure due to systolic or diastolic dysfunction and who are responding to therapy.

Stage D—advanced heart failure: patients in end-stage or refractory-to-therapy.

Many of the tests and procedures for accurately and successfully diagnosing, managing and treating heart failure are complex, expensive and available only at a hospital or other health-care setting. Methods for patients to manage heart failure at home or otherwise outside a health-care setting are less successful.

SUMMARY

A patient with pre-heart failure or heart failure can be managed in the home or a non-hospital setting. To help the patient manage heart failure, a means is provided to detect or monitor the patient's condition. The device can detect or monitor, for example, onset of acute decompensation, episodes of acute decompensation, episodes of hypoxia, episodes of myocardial ischemia, episodes of myocardial apoptosis or infarction, response to diuretic therapy, response to fluid intake, response to sodium intake, response to primary pharmacological agents (e.g., ACE inhibitor, β-blocker, aldosterone II receptor antagonist), and response to secondary pharmacological agents (e.g., hydralazine/isosorbide dinitrate). A patient in the pre-heart failure stage is often characterized with the presence of hypertension. Hypertension presents many of the same symptoms and in many instances is treated in the same manner as heart failure. Therefore, the methods and devices are also applicable to hypertensive patients. The device is also useful for patients at risk of a myocardial infarction, for example, a patient who has survived a first myocardial infarction and is at risk for future myocardial infarction.

A device allows the patient to perform frequent measurements of one or more biomarkers, collect information on signs and symptoms by paper chart or electronic diary, and, if necessary, to compute the measurement of biomarker(s) with other parameters such as signs and symptoms (e.g. breathlessness, cough, edema, decreased exercise tolerance, unexplained confusion or altered mental state, weight gain, fatigue, abdominal symptoms or signs related to ascites and hepatic engorgement, blood pressure, heart rate, variability of heart rate, and oxygen saturation). The biomarkers measured by the device can include, but are not limited to, markers of myocardial stretch, myocardial apoptosis or injury, myocardial ischemia, anemia, renal function, electrolytes, and markers of sodium balance. Because the test is simple enough to be carried out in the patient's home, daily measurements can be obtained and allow for an earlier notification of a detrimental change in the patient's condition than would otherwise be possible. Thus, the patient or a healthcare professional is able to review real-time data on the patient's pathophysiological state and response to therapy.

In one aspect, the present invention provides a means to determine the pathophysiological status and therapeutic response of a mammalian subject, comprising: a detector for measuring, in a sample taken from the subject, the level of a marker of:

left ventricular volume overload or myocardial stretch, renal function, myocardial apoptosis or injury, myocardial ischemia, electrolyte balance, sodium retention or inflammation.

The detector can be associated with a device for providing a display of the result of the measured parameters, and a means to manually or automatically input data from other measurements or observations or risk factors. The other measurements, observations or risk factors can including breathlessness, cough, edema, decreased exercise tolerance, unexplained confusion or altered mental state, weight gain, fatigue, abdominal symptoms or signs related to ascites and hepatic engorgement, blood pressure, heart rate, heart rate variability, oxygen saturation, age, gender, body mass index, frequency and volume on urination, dry cough, dry mouth, nausea, pain, fluid intake, salt intake, drug administration, exercise, weight control, and assessment of quality of life.

In another aspect, the present invention provides a means to input a series of preset or predetermined levels (decision points) for each parameter (e.g. a baseline level and a single or multiple action levels).

A baseline level for a marker may be assigned when the patient is stabilized. The baseline level can be a normal or target level. Relative changes with respect to the baseline value will then reflect improvements or deterioration in the patient's status allowing intervention by the patient or healthcare provider if necessary.

An action level for a marker is a level sufficiently separated from the baseline level to indicate a change in the patient's condition. This would result in the patient and, if necessary, the healthcare professional being alerted to a change in status. If appropriate, a recommended course of action can be relayed via the display or another means of communication. Relative changes relative to the action level would indicate improvements or further deterioration in the patient's condition.

The absolute level, or the rate of change, or the magnitude of change in the measured parameter can be compared to a predetermined level, such as a previously stored measurement or a preset action level.

The result of a measurement can be stored. The measurement can include raw data or interpreted data, such as absolute biomarker concentration, biomarker level relative to a preset action level, rate of change of the biomarker, magnitude of change of the biomarker, or any manually or automatically entered parameter.

The outcome of any measured or interpreted parameter or any manually or automatically entered parameter can be compared to the result for any other parameter.

The device can display and store in memory the findings of any of the above outcomes.

The device can relay stored data to a healthcare professional or other caregiver.

The device can be configured to determine when the user should perform a test or evaluate any other parameter.

The device can be configured to determine whether the user performed a test, administered a drug or any other intervention, or evaluated any other parameter.

The device can upload data from the instrument or to download data to the instrument.

In one aspect, a device for monitoring cardiac health includes a detector configured to measure, in a sample taken from a patient, a level of a biomarker selected from the group consisting of: a marker of left ventricular volume overload or myocardial stretch, a marker of myocardial apoptosis or injury, a marker of myocardial ischemia, a marker of inflammation, a marker of anemia, a marker of renal function, a marker of electrolyte balance, and a marker of sodium retention.

The device can be configured to provide an output to the patient. The detector can be configured to measure a level of a second biomarker. The second biomarker can be a marker of left ventricular volume overload or myocardial stretch, a marker of myocardial apoptosis or injury, a marker of myocardial ischemia, a marker of inflammation, a marker of anemia, a marker of renal function, a marker of electrolyte balance, or a marker of sodium retention. When the first biomarker is a marker of left ventricular volume overload or myocardial stretch and includes a natriuretic peptide, the second biomarker can be a marker of renal function.

The marker of left ventricular volume overload or myocardial stretch can include a natriuretic peptide. The marker of myocardial apoptosis or injury can include a troponin, urotensin, or a urotensin-related peptide. The marker of myocardial ischemia can include ischemia-modified albumin, oxygen-regulated peptide (ORP150), free fatty acid, Nourin-1, urotensin, or a urotensin-related peptide. The marker of inflammation can include E-selectin, P-selectin, intracellular adhesion molecule-1, vascular cell adhesion molecule-1, Nourin-1, interleukin-1β, interleukin-6, interleukin-8, interleukin-10, tumor necrosis factor-alpha, hs-CRP, neutrophils, or white blood cell count. The marker of anemia can include hemoglobin or hematocrit. The marker of renal function can include creatinine or Cystatin C. The marker of electrolyte balance can include $Na^+$ or $K^+$. The marker of sodium retention can include uroguanylin.

In certain circumstances, the first biomarker can be a marker of left ventricular volume overload or myocardial stretch, and the second biomarker can be a marker of renal function.

The device can include a probe for measuring a vital sign of the patient. The probe can measure a weight, a heart rate, variability of heart rate, a breathing rate, a blood pressure, a temperature, a blood oxygen saturation, or an electrocardiogram of the patient.

The device can include a memory capable of storing the results of a measurement of the level of the biomarker. The device can be configured to compare the result of a measurement of the level of the biomarker to a stored result. The memory is can store a threshold value of the level of the biomarker. The device can be configured to compare the result of a measurement of the level of the biomarker to the threshold value. The device can instruct or indicate to the patient or healthcare professional for the patient to commence, cease or alter a treatment plan when the measurement exceeds an upper or lower threshold value, or when the rate of change in the level of the biomarker between two or more measurements exceeds an upper or lower value. The treatment plan can include use of a diuretic. The device can further instruct the patient to obtain a measurement of a marker of renal function. The instruction can be made visually, on a display, printed or recoded on an output medium, or indicated by a sound or combination of sounds. An upper threshold is exceeded when the level of the biomarker is greater than the threshold value; and a lower threshold is exceeded when the level of the biomarker is less than the threshold value.

The device can include a display for displaying the results of the measurement, a patient query, or a patient instruction. The device can include an input device for supplying a response to a patient query. The device can be configured to provide a patient instruction in response to the results of the measurement. The instruction can be personalized.

In another aspect, a method of monitoring a patient includes measuring in a sample taken from a patient, a level of a biomarker selected from the group consisting of: a marker of left ventricular volume overload or myocardial stretch, a marker of myocardial apoptosis or injury, a marker of myocardial ischemia, a marker of inflammation, a marker of anemia, a marker of renal function, a marker of electrolyte balance, and a marker of sodium retention.

The method can include providing an output to the patient. The method can include measuring in a sample taken from a patient, a level of a second biomarker selected from the group consisting of: a marker of left ventricular volume overload or myocardial stretch, a marker of myocardial apoptosis or injury, a marker of myocardial ischemia, a marker of inflammation, a marker of anemia, a marker of renal function, a marker of electrolyte balance, and a marker of sodium retention.

The method can include recording the measured level of the biomarker. The method can include measuring the level of the biomarker at a later time, and comparing the recorded measured level to the later measured level. The method can include determining whether the patient is suffering from one or more symptoms associated with heart failure. The method can include measuring a weight, a heart rate, variability of heart rate, a breathing rate, a blood pressure, a temperature, a blood oxygen saturation, or an electrocardiogram of the patient.

In another aspect, a method of monitoring a patient includes making a single measurement or series of measurements of the level of a first biomarker of left ventricular volume overload or myocardial stretch; and providing, depending upon the levels of the first biomarker, an indication or instruction to the individual or healthcare professional to commence, cease or alter a diuretic treatment program. The method may also indicate to the user (e.g., patient or healthcare professional) to measure a level of a marker of renal function. Depending upon the results of the measurement of the level of the first biomarker and/or of the level of the marker of renal function, the method may also provide a further indication to alter the diuretic treatment plan. Altering the plan can include continuing or stopping the diuretic treatment program, increasing or decreasing the length or levels of the diuretic treatment program, and/or to commencing a diuretic treatment program using a further diuretic having a different potency. Thus the individual or healthcare professional can control the level of the first biomarker over time. Measurement of a marker of renal function provides an indication of the degree or extent of hydration of the individual, ensuring that the individual does not become too dehydrated as a consequence of taking a diuretic. An indication to commence a diuretic treatment program may be given when the level of the first biomarker exceeds a certain upper threshold or rate of change. Similarly, when the levels of the first biomarker fall below a certain lower threshold or rate of change, an indication may be given to stop or change the diuretic treatment program. The individual may then continue to monitor the levels of the said first biomarker to ensure that they remain within the upper and lower thresholds. Should the level of the first biomarker start to increase, the method may provide an indication to recommence diuretic therapy and monitoring for a marker of renal function. The absolute values of upper and lower thresholds and rates of change may be fixed or may vary depending upon the individual concerned. A device and a kit suitable for carrying out the above method are also provided.

In another aspect, a health care kit includes a test cartridge including a sample port and a first assay, wherein the first assay recognizes a marker of left ventricular volume overload or myocardial stretch, a marker of myocardial apoptosis or injury, a marker of myocardial ischemia, a marker of inflammation, a marker of anemia, a marker of renal function, a marker of electrolyte balance, or a marker of sodium retention, and a device including a detector configured to measure a level of the biomarker recognized by the assay. The first assay can include an antibody that recognizes a marker of left ventricular volume overload or myocardial stretch, a marker of myocardial apoptosis or injury, a marker of myocardial ischemia, a marker of inflammation, a marker of anemia, or a marker of sodium retention.

The kit can include a second test cartridge including a sample port and a second assay, wherein the second assay recognizes a marker of left ventricular volume overload or myocardial stretch, a marker of myocardial apoptosis or injury, a marker of myocardial ischemia, a marker of inflammation, a marker of anemia, a marker of renal function, a marker of electrolyte balance, or a marker of sodium retention. The second assay can include an antibody that recognizes a marker of left ventricular volume overload or myocardial stretch, a marker of myocardial apoptosis or injury, a marker of inflammation, a marker of myocardial ischemia, a marker of anemia, or a marker of sodium retention.

The first assay can include an antibody that recognizes a natriuretic peptide. The second assay can recognize a marker of renal function.

The details of one or more embodiments are set forth in the drawings and description below. Other features, objects, and advantages will be apparent from the description, the drawings, and from the claims.

BRIEF DESCRIPTION OF THE DRAWING

FIG. 1 is diagram illustrating a diagnostic device and an associated testing cartridge.

DETAILED DESCRIPTION

In a patient with heart failure, cardiac output is inadequate to meet the metabolic needs of the body, either at rest or with exercise. An increase in cardiac filling pressure or volume usually occurs as well. Heart failure is most commonly due to left ventricular systolic dysfunction (LVSD) where the myocardium fails to contract normally and the left ventricle is usually dilated. As the disease progresses, the body responds to the diminished cardiac output through activation of the renin-angiotensin-system (RAS) causing arterial vasoconstriction, enhanced sodium reabsorption, and volume expansion. There is an increase in presynaptic stimulation of sympathetic nerves to enhance norepinephrine release, which is deleterious in the long-term for the patient. These effects, which are mediated by angiotensin II binding to the $AT_1$ receptor, are immediate and are compensatory changes that develop to augment cardiac output and increase perfusion pressure to vital organs. In addition to these immediate hemodynamic effects, angiotensin II also causes cardiac remodeling through fibroblast and myocyte proliferation. Remodeling involves increases in left ventricle volume and mass, as well as changes in conformation that ultimately lead to diastolic and systolic dysfunction. Another immediate effect of angiotensin II relevant to the heart failure patient is an increased thirst caused by the release of arginine vasopressin which can exacerbate the fluid retention.

The overall treatment plan for a patient with hypertension, pre-heart failure (Stage B) or heart failure (Stages C or D) includes careful management of pharmacological therapy, diet and lifestyle. The primary goals are prolongation of the patient's life by preventing, slowing, halting, or reversing the progressive condition, relief of the patient's symptoms, and improvement in the patient's quality of life.

Hypertension is defined by the National Heart Lung and Blood Institute as systolic blood pressure of 140 mm Hg or greater, or diastolic blood pressure of 90 mm Hg or greater. Current treatments are very effective in improving cardiovascular health to decrease the incidence and severity of hypertension complications. However, only about one quarter of hypertensive patients adequately control their disease. Chronic hypertension is a "silent killer" with no symptoms to remind of the need for continuous treatment. Compliant hypertension therapy with favorable outcomes depends on strong initial education backed by ongoing reinforcement of treatment benefits. Unfortunately, the widespread use of arterial blood pressure measurement in these patients is known to be a poor predictor of mortality. The ideal measurement is left ventricular filling pressure because this elevated pressure is part of the process that leads to left ventricular hypertrophy and eventually heart failure. However, such a measurement is not routinely practical. An alternative approach would be to measure a marker of left ventricular volume overload to give an indication of increased ventricular pressure.

Symptoms and signs of heart failure and a worsening condition include breathlessness, cough, edema in the lower extremities, decreased exercise tolerance, unexplained confusion or altered mental state, weight gain, fatigue, and abdominal symptoms or signs related to ascites and hepatic engorgement.

Important classes of drugs used in the treatment of heart failure include ACE inhibitors, beta-blockers, aldosterone receptor blockers, and diuretics. ACE inhibitors, beta-blockers, and aldosterone receptor blockers reduce morbidity/mortality whereas diuretics improve the patient's quality of life (primarily by reducing symptoms). The patient's lifestyle can have a major influence on the efficacy of the drug regimen through poor compliance with drug administration and poor diet. For example, fluid overload can blunt the therapeutic effects and fluid depletion can exacerbate the adverse effects of other drugs. Both situations can lead to dangerous outcomes.

The stages of the treatment plan include therapy optimization and maintenance. In the optimization stage the patient should first be stabilized if there is evidence of fluid overload and then appropriate additional pharmacotherapy should be introduced.

A patient's control of fluid balance can be achieved with use of a diuretic and, if necessary, restriction of salt and fluid intake. Diuretics need to be monitored to track electrolyte disturbances, dehydration, and excessive water retention. Inappropriate management of diuretics has a negative impact on the effectiveness of concomitant drug therapies. Diuretic therapy can be self-managed by the patient. The patient monitors his or her weight daily and if significant weight gain occurs over a period of a few days then the patient can double the diuretic dose (e.g., increase Furosemide from 40 mg bid to 80 mg bid) and, if necessary, add a second diuretic (e.g., Metolazone) for a short time until the normal dry weight is resumed. This strategy should be used whenever the patient experiences weight gain of 3 pounds in 2 days, or five pounds in one week.

When the patient is euvolemic, angiotensin II activity should be reduced by inhibiting the action of ACE on angiotensin I using an ACE inhibitor. Alternatively, the binding of angiotensin II to its $AT_1$ receptor can be blocked using an angiotensin receptor blocker (ARB). ACE inhibitors are usually started at a low dose and then up-titrated over 2-3 week intervals as tolerated either symptomatically or hemodynamically. Careful attention to tolerance is monitored by laboratory parameters (e.g., serum creatinine and serum electrolytes), blood pressure, and symptomatic side-effects (e.g., development of a dry cough).

β-blockers are widely used as an additional component of the treatment plan to prevent norepinephrine-mediated effects. Norepinephrine is toxic to cardiac cells, stimulates apoptosis, and has a negative effect on cardiac structure by stimulating myocyte hypertrophy and fibroblast production, part of the remodeling process. β-blockers should be initiated cautiously in certain patients. Assessment of tolerance is usually through measurement of heart rate and blood pressure.

As described above, effective pharmacological treatments exist that can slow progression of the disease and extend the patient's life. However, these drugs are rarely used at their therapeutic levels because physicians have no easily accessible method to demonstrate effectiveness of increased doses of the drug. Instead, side effects (which are manageable by careful adjustment in other medications, such as diuretic dose) often result in drugs being used at sub-optimal levels. Further, patients often have poor compliance with their drug therapy. Even for those patients who are able to self-manage their diuretic therapy, weight tracking is an insensitive indicator of increasing volume overload.

Poor compliance by the patient to diet (fluid intake and salt intake) and drug treatment is the main reason for episodes of acute decompensation, independent of whether the patient is receiving appropriate pharmacological therapy. During fluid retention, plasma volume can increase by as much as 70% during an episode of decompensation. Such life-threatening events require hospitalization and aggressive management. Detecting an impending event (such as by measuring a change in a biomarker) would allow avoidance of dangerous events by careful adjustment of diuretics and diet.

In the event of fluid retention, fluid overload will cause left ventricular volume overload, putting strain on the heart. Ultimately, cardiac output is reduced, causing fluid build-up in the lungs resulting in pulmonary congestion. On the other hand, in the event of fluid depletion, the condition of dehydration will arise. In either case, a further consequence can be an unfavorable change to the levels of electrolytes.

Ideally, the health care provider has information on left ventricular volume overload, fluid retention, fluid depletion, electrolyte balance, and renal function. Information on signs and symptoms will also help the caregiver manage the patient's treatment.

Measurement of left ventricular volume overload can be obtained using hospital-based technologies, such as chest X-ray, electrocardiography, echocardiography, radionuclide imaging and dilutional analysis. A chest X-ray will reveal cardiomegaly, venous congestion, and chamber enlargement.

Electrocardiography will reveal ventricular hypertrophy, and atrial enlargement. Echocardiography is used to determine systolic and diastolic left ventricular performance, chamber size and shape, wall thickness, ejection fraction (cardiac output), and pulmonary artery and ventricular filling pressures. Radionuclide scans provide more precise measurement of ejection fraction but require venous injection of radioactive material. Fluid retention can be evaluated using dilutional analysis: the patient is injected with a tracer molecule and the resultant dilution of the tracer in the patient's blood provides an estimate of plasma volume.

Obtaining these types of measurements requires access to costly equipment, expert knowledge, and for the patient, a visit to the hospital or clinic. Performing regular visits for serial assessment of the patient's condition is therefore impractical due to limitations such as patient access, long waiting lists, and high cost.

Further, these measurements provide information only on the underlying macro-physiology but no specific information on what is happening at the cellular level with respect to neurohormonal control, sympathetic neurotransmitter control, and the process of cardiac remodeling.

Outside the use of aforementioned physical measurements carried out in hospital or clinic, a patient's condition can be assessed according to the New York Heart Association four-stage classification where the patient's functional capacity is categorized as follows:

Class I: Patients exhibit symptoms only at exertion levels.
Class II: Patients exhibit symptoms with ordinary exertion.
Class III: Patients exhibit symptoms with minimal exertion.
Class IV: Patients exhibit symptoms at rest.

However, there is only a weak correlation between signs and symptoms (e.g. shortness of breath, non-specific fatigue and edema) and severity of the underlying left ventricular dysfunction. Therefore, the cardiologist relies on infrequent physical measurements often only performed at the time of hospital presentation or during a hospital stay. The generalist physician and healthcare team who deliver routine care to the patient have access to less information on which to make clinical decisions on patient care.

The measurement of blood chemistries (for example, electrolytes, creatinine, hemoglobin, and blood urea nitrogen) is a standard component of the patient's care plan. These are laboratory tests that require a blood specimen to be drawn at the point of care (i.e., in the physician's office, the heart failure clinic, or the hospital). Consequently, laboratory tests are performed relatively infrequently (e.g., every 3 months during a scheduled visit or when the patient is being assessed because of a deteriorating condition). Therefore, these laboratory tests do not predict or detect changes in the patient's condition rapidly enough to prevent an adverse event, such as acute decompensation. Nor are they performed often enough to enable optimal drug titration.

A consequence of sub-optimal control of the patient's condition is a high incidence of hospital admission and readmission, most often as a result of fluid retention leading to left ventricular volume overload.

The main causes of fluid retention are poor dietary control (uncontrolled salt and fluid intake), use of sub-optimal doses of medications, and poor compliance with the treatment regimen. The sequence of events that result in hospitalization often occurs in the home, outside the care setting, away from sophisticated technologies (e.g., echocardiography), laboratory tests, and the expert eye of the caregiver.

The patient is encouraged to take on some responsibility for monitoring his or her condition at home by complying with the treatment plan and checking for signs of left ventricular volume overload. Doing so can reduce the occurrence of events that might result in hospitalization. The only current objective measurements that have been evaluated for use in the patient's home are daily weights, heart rate, and oxygen saturation.

To perform daily weights, the patient is instructed to weigh him/herself every morning, before breakfast, before taking any medications or liquids, after urinating, wearing the same type of clothes, without shoes, on the same scale (in the same location each day on a flat, hard surface). Daily weight is recorded in a notebook and, if there has been a gain in weight of 3 pounds in 2 days, or 5 pounds in one week, the patient is instructed to inform his or her healthcare team.

Alere Medical Incorporated (of Reno, Nev., USA) developed the Alere® Heart Monitoring Program featuring the DayLink® monitor. The Alere DayLink® monitor is a biometric measurement device with an interactive display and communications appliance. The DayLink monitor gathers the patient's weight and heart failure symptoms. To use the DayLink® monitor, a patient just steps onto the platform. Once a patient's weight has been captured, the DayLink® monitor asks physician-specified questions about the patient's symptoms, via audible voice and visual display. The patient answers the questions by pressing YES or NO keys.

A major disadvantage of this approach is the insensitivity of weight measurement. In controlled clinical studies, daily weights have been shown to be reasonably effective at identifying fluid overload and helping the patient remain compliant with his or her treatment plan. In practice, however, daily weights are either not utilized or are too inaccurate to be useful. For example, by the time that a significant change in weight has been detected, the patient may already be in need of hospitalization.

Patients with heart failure suffer from a high probability of hypoxia, myocardial ischemia, and myocardial infarcts. There is currently no means to track the occurrence of these events in a patient's home. Failure to detect these events at an early stage results in the onset of deleterious consequences, worsened prognosis, and increased resource utilization.

Consequently, the quality of care available to heart failure patients and their resultant prognosis is lower than would be possible if more objective and predictive measurements were available in the home or remote care-setting to steer the treatment plan.

Markers of Left Ventricular Volume Overload and Myocardial Stretch

Measurement of neurohormones has been explored by the research community for several decades. Biomarkers that have been investigated include the natriuretic peptides, A-type-(ANP), B-type-(BNP), and C-type-(CNP) natriuretic peptide and their N-terminal prohormones (N-ANP, N-BNP, and N-CNP). ANP (also known as atrial natriuretic peptide) and its inactive form, N-ANP, have been described in, for example, Hall, *Eur J Heart Fail,* 2001, 3:395-397, which is incorporated by reference in its entirety.

BNP (the active peptide) and N-BNP (the inactive peptide) are found in the circulation. Both peptides are derived from the intact precursor, proBNP, which is released from cardiac myocytes in the left ventricle. Increased production of BNP (or N-BNP; the abbreviation BNP refers to either form of the B-type natriuretic peptide throughout this document) is triggered by myocardial stretch, myocardial tension, and myocardial injury. Studies have demonstrated a positive correlation between circulating levels of BNP, left ventricular volume overload (e.g., left ventricular end diastolic pressure), and an inverse correlation to left ventricular function (e.g., left ventricular ejection fraction and left ventricular mass index).

Measurement of natriuretic peptides, in particular BNP, has been mainly limited to diagnosis of acute decompensation in suspected heart failure patients in the Emergency Department in a hospital setting, providing a prognosis for patients with acute decompensation during hospitalization, and therapy tracking of patients with acute decompensation prior to discharge from hospital. More recent work has investigated the role of BNP during clinic visits and demonstrated that BNP correlates with improvement in the patient's functional status. See, for example, Kohno M; *Am J. Med.* 1995 March;98(3):257-65, which is incorporated by reference in its entirety. However, testing was infrequent—tests were conducted at baseline, 6 months, and 12 months. Similarly, the study by Kawai (Kawai K; *Am Heart J.* 2001 June;141(6): 925-32, which is incorporated by reference in its entirety) was limited to testing intervals at baseline, 2 months, and 6 months. Studies by Troughton, Latini and McKelvie also used a testing interval of 4 months or greater (see Lancet 2000, 355:1126-30; *Circulation* 2002 November 5;106(19): 2454-8; and *Circulation* 1999 Sep. 7;100(10):1056-64, respectively, each of which is incorporated by reference in its entirety).

The shortest testing interval was used by Murdoch (Murdoch DR; *Am Heart J.* 1999 December;138(6 Pt 1):1126-32, which is incorporated by reference in its entirety). Murdoch used a testing interval of every two weeks, but the study did not consider event detection, safe titration of therapy (by using a GFR marker; see below) or an out-patient or home-care setting.

The only study to have used a higher testing frequency (Braunschweig, F; *J Cardiovasc Electrophysiol.* 2002 January;13(1 Suppl):S68-72, which is incorporated by reference in its entirety) investigated the correlation of BNP to weight gain and hemodynamics. A major limitation of this study was the long testing interval of weekly blood draws and again the failure to consider the use of BNP and a GFR marker in a home care setting—in fact, the purpose of the study was to evaluate an implanted hemodynamic sensor and compare this to weight tracking.

There is a danger that the patient or caregiver will drive the patient to a state of under-hydration if they rely on BNP levels alone. Furthermore, a target BNP level for one patient might be unsuitable for another patient because of factors such as age, gender, body mass index, extent of hypertrophy, etc.

In the studies discussed above, the patient and their caregiver did not have access to objective data at a suitable testing interval to allow the prevention of future events (e.g. acute decompensation), rapid drug optimization (e.g. ACE inhibitors, β-blockers, aldosterone receptor blocker), and controlled dose adjustment of diuretics without putting the patient at risk.

Markers of Myocardial Apoptosis or Injury

Markers of myocardial apoptosis provide information on cardiac remodeling, which is an effect of left ventricular volume overload. Measurement of increased myocyte apoptosis arising from excessive myocardial stretch, norepinephrine toxicity, and other proposed mechanisms provide information on cardiac remodeling. Suitable markers include cardiac troponins, including the isoforms troponin I and troponin T (TnI and TnT, respectively), as well as urotensin in all its forms and urotensin-related peptides. Measurement of troponin has traditionally been used to provide a diagnosis of myocardial injury or infarction, distinct from the process of apoptosis. A sensitive immunoassay for a troponin isoform can allow a healthcare provider to obtain information on the extent of myocyte apoptosis and myocyte damage induced by the aforementioned mechanisms or consistent with myocardial ischemia and infarction.

Cardiac troponin levels are frequently above normal values in several disease states in which myocardial necrosis is not a prominent aspect, particularly in pulmonary embolism, heart failure, liver cirrhosis, septic shock, renal failure and arterial hypertension. Sub-clinical myocardial necrosis and increased myocardial apoptosis has been postulated to be the cause of the phenomenon. Increased troponin levels may be the result of ventricular dilatation or hypertrophy. Troponin may act as a marker of myocardial strain, injury, and increased apoptosis (e.g., during acute decompensation or chronic worsening pre-heart failure, heart failure, and hypertension). Apoptosis contributes to myocardiocyte loss in cardiac disease and may have a pathophysiologic role in left ventricular (LV) remodeling. Heart failure is associated with an increase in apoptosis rate and is significantly correlated with parameters of progressive left ventricle remodeling. Low levels of troponin in the circulation correlate with apoptosis rate.

Elevated levels of troponin without elevated levels of creatine kinase is thought to be due to release of troponin from myocardial cells without the disruption of myocardial cell plasma membrane.

Chen measured troponin in the plasma of patients with heart failure. See Chen YN, *Ann Clin Biochem.* 1999 July;36 (Pt 4):433-7, which is incorporated by reference in its entirety. Elevated plasma troponin concentrations were found in 89% of heart failure patients while plasma creatine kinase-MB (CK-MB) showed no significant difference. During follow-up, serial measurements of cardiac TnI and CK-MB were performed. In heart failure patients, improvement of the clinical profile was associated with declining troponin concentrations, while deterioration of heart function was closely related to increasing troponin concentrations. Cardiac damage relates to functionally overloaded myocytes and troponin may be a sensitive marker both for early detection of myocyte damage and for monitoring of function and prognosis in patients with heart failure. Chen demonstrated that plasma troponin levels that returned to normal in patients whose heart failure was successfully treated had better outcomes than in patients whose troponin remained elevated.

Horwich demonstrated that troponin is elevated in severe heart failure and may predict adverse outcomes (Horwich, TB; *Circulation.* 2003 August 19;108(7):833-8, which is incorporated by reference in its entirety). They presented data on 238 patients with advanced heart failure who had troponin assay drawn at the time of initial presentation. Patients with acute myocardial infarction or myocarditis were excluded from analysis. Troponin was detectable (greater than or equal to 0.04 ng/mL) in serum of 117 patients (49.1%). Patients with detectable troponin levels had significantly higher BNP levels and more impaired hemodynamic profiles, including higher pulmonary wedge pressures and lower cardiac indexes. A significant correlation was found between detectable troponin and progressive decline in ejection fraction over time.

Detectable troponin was associated with increased mortality risk. Troponin used in conjunction with BNP improved prognostic value. Therefore, troponin is associated with impaired hemodynamics, elevated BNP levels, and progressive left ventricular dysfunction in patients with heart failure.

Monitoring troponin to detect myocardial infarction in the context of ischemia is already accepted practice (see, for example, Apple FS, European Society of Cardiology and American College of Cardiology guidelines for redefinition of myocardial infarction: how to use existing assays clinically and for clinical trials; *Am Heart J.* 2002 December; 144(6): 981-6, which is incorporated by reference in its entirety).

Therefore, routine measurement of troponin is valuable in the management of the heart failure patient. Serial tracking of troponin will enable information on the patient's condition (whether stable, worsening, or improving) to be determined and will also provide information on future prognosis.

Markers of Inflammation

Inflammation markers can provide information about a patient's condition. A marker of inflammation can be used to predict sudden unexpected death. The marker can be non-specific (i.e., a marker of general inflammation), or specific (i.e., a marker indicating cardiac or vascular inflammation). The marker can be a soluble adhesion molecule (e.g., E-selectin, P-selectin, intracellular adhesion molecule-1, or vascular cell adhesion molecule-1), Nourin-1, a cytokine (e.g., interleukin-1β, -6, -8, and -10 or tumor necrosis factor-alpha), an acute-phase reactants (e.g., hs-CRP), neutrophils, and white blood cell count.

Markers of Anemia

Markers of anemia can also be valuable in tracking heart failure patients. According to one study, heart failure patients with low hematocrits had a significantly higher risk of mortality than those with hematocrit>42% (see Kosiborod, M., et al. *Am. J. Med.* 2003, 114: 112-119, which is incorporated by reference in its entirety). For example, a hemoglobin level or hematocrit measurement can be used as a marker of anemia.

Markers of Myocardial Ischemia

Markers of myocardial ischemia provide independent information on cardiac output, thrombus formation and embolization, and vascular blood flow. Measurement of such markers (e.g., ischemia-modified albumin, oxygen-regulated peptide (ORP150), free fatty acid, Nourin-1, urotensin in all its forms and urotensin-related peptides, and other known markers) provide an indication of onset of ischemia, magnitude of ischemia, and natural or induced reperfusion.

Markers of Renal Function

The easiest way to measure the glomerular filtration rate (GFR) is with creatinine (Robertshaw M, Lai KN, Swaminathan R. Br *J Clin Pharmacol* 1989;28:275-280, which is incorporated by reference in its entirety). The rate of creatinine addition to the body is proportional to body muscle mass. The rate of creatinine removal is proportional to the concentration in the plasma and the rate of glomerular filtration. For example, a decrease of GFR from 120 mL/min to 60 mL/min would increase the plasma creatinine from 1.0 mg/dL to 2.0 mg/dL. Thus, changes in GFR are mirrored by reciprocal changes in the serum creatinine. Because serum creatinine multiplied by GFR equals the rate of creatinine production, a decrease in the GFR by 50% will cause the serum creatinine to increase by a factor of two at steady-state. Using only a serum or plasma creatinine measurement, the GFR, in mL/min, can be estimated using the formula: GFR=(140−age)×weight (kg)/0.825×plasma creatinine (μmol/L).

Markers of renal function should be monitored regularly in patients on ACE inhibitors, angiotensin II receptor inhibitors, and diuretics. A limited elevation in creatinine level (30 percent or less above baseline) was seen following initiation of therapy with an ACE inhibitor or angiotensin II receptor inhibitors. The increase usually occurred within two weeks of therapy. Regardless of the creatinine value, manifestations of renal failure were not apparent until the GFR was well below 30 mL per minute. Patients with the greatest degree of renal insufficiency experienced the greatest protection from renal disease progression. Hence, upon initiation of an ACE inhibitor or angiotensin II receptor inhibitor, GFR should be monitored, but a decrease is not a reason to withdraw therapy.

The study by Lee (Lee SW; *Am J Kidney Dis.* 2003 June; 41(6): 1257-66, which is incorporated by reference in its entirety) revealed that BNP levels are insensitive to under-hydration in patients on hemodialysis. Lee was evaluating whether BNP might be used to assess hydration status in a patient undergoing aggressive hemodialysis. When these findings are applied to the process of diuresis using either intravenous or oral diuretic therapy, one would realize that BNP cannot be used to detect a state of over-diuresis which could be life threatening. Consequently, routine measurement of a glomerular filtration rate marker is necessary to determine whether the patient is at risk of under-hydration through over-use of diuretic therapy.

Several biochemical methods exist for the measurement of GFR. Generally, these measure the level of an analyte that is metabolized at a constant rate, so that an increase in circulating levels of the analyte indicates renal failure. Suitable such analytes include creatinine and Cystatin C. See, for example, Newman, DJ, *Ann Clin Biochem.* 2002 March;39(Pt 2):89-104; and Pyrrone RD et al, *Clin Chem.* 1992 October;38(10): 1933-53:, each of which is incorporated by reference in its entirety. Measurement of GFR with creatinine (plasma or serum creatinine) can be achieved with the Cockroft and Gault equation to adjust for age, weight, and gender.

An alternative measurement of GFR can be achieved with Cystatin C. Cystatin C has a low molecular weight and is filtered freely at the glomerular membrane. Cystatin C has been proposed as an alternative and superior marker to serum creatinine. Cystatin C is produced by all nucleated cells and catabolized by renal tubular cells. Its rate of production is constant and is not affected by muscle mass, inflammation, and it does not have a circadian rhythm.

Cystatin C was found to be more specific than serum creatinine in evaluating renal function with a tighter distribution of values around the regression line (Mussap, M; *Kidney International, Vol* 61 (2001), pp 1453-1461, which is incorporated by reference in its entirety). Mussap also reported that Cystatin C rises earlier and more rapidly than serum creatinine as GFR decreases—it has higher sensitivity than both serum creatinine and GFR derived from the Cockroft-Gault equation. commercial test for serum Cystatin C is available from Dade Behring (nephelometric assay; N-latex Cystatin C Assay; 6 minute test).

Markers of Electrolyte Balance

Electrolyte balance is the condition where a patient's electrolytes (for example, soluble ions such as $Na^+$ and $K^+$) are in the normal concentration range. The subject may be a heart failure patient with a stable condition, a heart failure patient with an unstable condition, a patient with mild, moderate, or advanced hypertension, or a patient with recent myocardial infarction. Typical values of normal fluid and electrolyte balance are as follows and are dependent upon the age and sex of the individual: for an average 70 kg man the total body water is typically 42 L (60% of body weight), with 28 L being in the intracellular and 14 L in the extracellular compartments. The plasma volume is 3 L and the extravascular volume is 11 L. Total body $Na^+$ is typically 4200 mmol (50% in extracellular fluid, (ECF)) and the total body $K^+$ is typically 3500 mmol (about 50-60 mmol in ECF). The normal osmolality of ECF is 280-295 mosmol/kg.

Hypokalemia is a common adverse effect of diuretic therapy and may also increase the risk of digitalis toxicity. Hence, plasma or serum potassium levels should be routinely measured in heart failure patients in order to avoid such undesirable side effects. Potassium is typically measured using an ion-selective electrode (e.g. i-STAT, i-STAT Corp.)

Markers of Sodium Retention

Markers of sodium retention or excessive sodium intake can provide an estimate of sodium retention, electrolyte balance, and sodium consumption. One suitable marker is uroguanylin, which is an intestinal natriuretic hormone and functions as an endocrine modulator of sodium homeostasis. In a patient with congestive heart failure, levels of uroguanylin measured in urine are known to be substantially higher than in controls. The increased urinary uroguanylin excretion in patients with heart failure may be an adaptive response. The urinary excretion of uroguanylin is significantly higher in the presence of a high salt diet and significantly correlated with urinary sodium. Measurement of uroguanylin can provide unique information on sodium homeostasis and the patient's status. Such measurement may be used to make decisions on intake of fluid and sodium to avoid adverse events.

Diagnostic Device

A homecare diagnostic device enables a heart failure patient and health care provider to safely optimize the care plan, and to track and steer the patient's response to therapy, diet, and lifestyle. The device can measure and record the levels of one or more biomarkers, record patient input regarding signs and symptoms of disease, provide feedback to the patient, and provide recorded results to a health care provider.

Using the device, the patient's condition can be monitored remote from a dedicated health care facility, such as doctor's office or hospital. Providing information to optimally manage the patient's condition helps to prevent left ventricular volume overload. The information can also help to predict the onset of acute decompensation arising through left ventricular volume overload, thereby allowing early intervention. Use of the device can ensure that interventions aimed at reducing fluid volume do not over-compensate, resulting in dehydration. The device can help the health care provider measure the effectiveness of both pharmacological and non-pharmacological aspects of the care plan, and to monitor the progression of the disease. The device can also aid in assessing the patient's compliance to therapy and future prognosis.

The biomarkers measured by the device can include a marker of left ventricular volume overload or myocardial stretch, a marker of myocardial apoptosis or injury, a marker of myocardial ischemia, a marker of inflammation, a marker of anemia, a marker of renal function, a marker of electrolyte balance, or a marker of sodium retention. In addition, the device can include probes for measuring the patient's vital signs, such as weight, temperature, heart rate, variability of heart rate, breathing rate, blood pressure, and blood oxygen saturation (measured, for example, by pulse oximetry). The device can record electrical measurements, such as an electrocardiogram, from the patient. The device can present queries to the patient and record the patient's responses. The queries can relate to the patient's condition, such as whether the patient is suffering any symptoms or when medication was taken.

In general, the patient will use the device on a regular basis as instructed by a caregiver. For example, the patient may use the device daily, every other day, weekly, or on another appropriate interval. Under certain circumstances, fewer than all available tests will be performed. For example, a patient may perform a blood pressure measurement on a daily basis, but measure a marker of left ventricular volume overload or myocardial stretch on a weekly basis. Based on the results of the tests, the device can respond with instructions for the patient. The instructions can be configured based on a treatment algorithm. The algorithm can be adjusted to suit the needs of the patient. For example, if a health care provider can enter information specific to a particular patient (such as a threshold value for a biomarker) into the device.

The biomarkers can be measured in a sample. The sample is taken from the patient and can be a sample of blood, plasma, serum, saliva or urine. In one embodiment, the sample is a blood sample. Such a sample may be taken by the patient by, for example, collecting a blood sample having a volume of less than one microliter up to a volume of several hundred microliters following puncture of the skin with an appropriate lancing device. The biomarkers monitored can be detected using, for example, an immunoassay, a biosensor, an ion-selective electrode, or another suitable technology.

For example, the markers can be detected using an immunoassay. An immunoassay is performed by contacting a sample from a subject to be tested with an appropriate antibody under conditions such that immunospecific binding can occur if the marker is present, and detecting or measuring the amount of any immunospecific binding by the antibody. Any suitable immunoassay can be used, including, without limitation, competitive and non-competitive immunoassay systems or ligand-binding systems known to one skilled in the art.

For example, a marker can be detected in a fluid sample by means of a one-step sandwich assay. A capture reagent (e.g., an anti-marker antibody) is used to capture the marker. Simultaneously, a directly or indirectly labeled detection reagent is used to detect the captured marker. In one embodiment, the detection reagent is an antibody. Such an immunoassay or another design known to one skilled in the art can be used to measure the level of an aforementioned biomarker in an appropriate body fluid.

A GFR marker (e.g. serum creatinine) can be measured using a biosensor, an enzymatic assay, or amperometrically. See, for example, Erlenkotter A, *Anal Bioanal Chem.* 2002 January;372(2):284-92; Leger F, *Eur J Cancer.* 2002 January; 38(1):52-6; and Tombach B, *Clin Chim Acta.* 2001 October; 312(1-2):129-34, each of which is incorporated by reference in its entirety.

The measurement of a biomarker by both immunoassay and biosensor (e.g. calorimetrically) has been demonstrated by Metrika with their patented MODM™ (Micro Optical Detection Method) technology. This integrates miniaturized digital electronics, micro-optics and solid-state chemistries into an easy to use, low-cost, single-use instrument. MODM technology is designed for simultaneous measurement of immunodiagnostic and general chemistries in less than ten minutes. Ostex International Inc. has used the same technology to develop the OSTEOMARK NTx Point-of-Care (POC). This is a disposable single use device that provides a normalized measurement of the bone marker 'NTx' by measuring NTx and creatinine levels in a sample and then calculating the ratio result. The POC is intended for use in a physician's office and takes 5 minutes to process.

The device can be included in a diagnostic kit, which can optionally include one or more of the following: instructions for using the kit for event detection, diagnosis, prognosis, screening, therapeutic monitoring or any combination of these applications for the management of patients with pre-heart failure, heart failure, or hypertension; a disposable testing cartridge containing the necessary reagents to conduct a test; or an instrument or device that measures the result of biomarker testing and optionally, allows manual or automatic input of other parameters, storage of said parameters, and evaluation of said parameters alongside or separate from the evaluation of the measured biomarkers.

The testing cartridge or cartridges supplied in the kit allow the user to measure as a minimum, a marker of left ventricular volume overload or myocardial stretch and optionally a measurement of a marker of renal function, a measurement of a marker of myocardial apoptosis, a measurement of a marker of myocardial ischemia, a measurement of a marker of myocardial injury, a measurement of a marker of anemia, a measurement of a marker of electrolyte balance, and a marker of sodium retention.

Preferably, the testing cartridge or testing cartridges allow the sequential or serial measurement of a marker of left ventricular volume overload or myocardial stretch and a marker of renal function.

The testing cartridge or testing cartridges allow the sequential or serial measurement of a marker of left ventricular volume overload or myocardial stretch, a measurement of a marker of renal function, a measurement of a marker of myocardial apoptosis or injury, a measurement of a marker of myocardial ischemia, a measurement of a marker of inflammation, a measurement of a marker of anemia, a measurement of a marker of electrolyte balance, and a marker of sodium retention. A combination cartridge can test two or more different markers from a single sample.

The instrument (durable or disposable), at a minimum, measures the result of biomarker testing and optionally, allows manual or automatic input of other parameters, storage of said parameters, and evaluation of said parameters with or separate to the measured biomarkers.

Referring to FIG. 1, diagnostic device 100 includes display 120 and input region 140. The display 120 may be used to display images in various formats, for example, joint photographic experts group (JPEG) format, tagged image file format (TIFF), graphics interchange format (GIF), or bitmap. Display 120 can also be used to display text messages, help messages, instructions, queries, test results, and various information to patients. In some implementations, display 120 supports the hypertext markup language (HTML) format such that displayed text may include hyperlinks to additional information, images, or formatted text. Display 120 can further provide a mechanism for displaying videos stored, for example in the moving picture experts group (MPEG) format, Apple's QuickTime format, or DVD format. Display 120 can additionally include an audio source (e.g., a speaker) to produce audible instructions, sounds, music, and the like.

Input region 140 can include keys 160. In one embodiment, input region 140 can be implemented as symbols displayed on the display 120, for example when display 120 is a touch-sensitive screen. Patient instructions and queries are presented to the patient on display 120. The patient can respond to the queries via the input region. Device 100 also includes cartridge reader 180, which accepts diagnostic test cartridges for reading. The cartridge reader 180 measures the level of a biomarker based on, for example, the magnitude of a color change that occurs on a test cartridge 400. Device 100 also includes probe connections 200, which connect probes (e.g., a probe of weight, temperature, heart rate, variability of heart rate, breathing rate, blood pressure, or blood oxygen saturation) to the device.

Device 100 further includes a communication port 220. Communication port 220 can be, for example, a connection to a telephone line or computer network. Device 100 can communicate the results of patient tests to a health care provider from a remote location. Likewise, the health care provider can communicate with the device 100 (e.g., to access stored test results, to adjust device parameters, or send a message to the patient).

Cartridge 400 is shown with two testing zones 420. In general, a cartridge can include 1, 2, 3, 4, or 5 or more testing zones. Each testing zone 420 can test the level of a biomarker. Each testing zone 420 includes a sample input 440, a control result window 460 and a test result window 480. In one embodiment, the cartridge 400 is an immunochromatographic test cartridge. Examples of immunochromatographic tests and test result readers can be found in, for example, U.S. Pat. Nos. 5,504,013; 5,622,871; 6,235,241; and 6,399,398, each of which is incorporated by reference in its entirety.

A patient can use device 100 for testing and recording the levels of various biomarkers that provide information about the patient's health. Various implementations of diagnostic device 100 may access programs and/or data stored on a storage medium (e.g., video cassette recorder (VCR) tape or digital video disc (DVD); compact disc (CD); or floppy disk). Additionally, various implementations may access programs and/or data accessed stored on another computer system through a communication medium including a direct cable connection, a computer network, a wireless network, a satellite network, or the like.

The software controlling the diagnostic device and providing patient feedback can be in the form of a software application running on any processing device, such as, a general-purpose computing device, a personal digital assistant (PDA), a special-purpose computing device, a laptop computer, a handheld computer, or a network appliance.

A diagnostic device may be implemented using a hardware configuration including a processor, one or more input devices, one or more output devices, a computer-readable medium, and a computer memory device. The processor may be implemented using any computer processing device, such as, a general-purpose microprocessor or an application-specific integrated circuit (ASIC). The processor can be integrated with input/output (I/O) devices to provide a mechanism to receive sensor data and/or input data and to provide a mechanism to display or otherwise output queries and results to a service technician. Input device may include, for example, one or more of the following: a mouse, a keyboard, a touch-screen display, a button, a sensor, and a counter.

The display 120 may be implemented using any output technology, including a liquid crystal display (LCD), a television, a printer, and a light emitting diode (LED). The computer-readable medium provides a mechanism for storing programs and data either on a fixed or removable medium. The computer-readable medium may be implemented using a conventional computer hard drive, or other removable medium such as those described above with reference to. Finally, the system uses a computer memory device, such as a random access memory (RAM), to assist in operating the diagnostic device.

Implementations of a diagnostic device can include software that directs the patient in using the device, stores the result of biomarker measurements, determines whether a tested biomarker level requires medical attention for the patient, instructs the patient in adjusting or maintaining therapy, and communicates the patient's information to his or her caregiver. Patients suffering from, for example, heart failure or hypertension, or patients at risk of a myocardial infarction can use the device.

The device 100 can provide access to applications such as a medical records database or other systems used in the care of patients. In one example, the device connects to a medical records database via communication port 220. Device 100 may also have the ability to go online, integrating existing databases and linking other websites. Online access may also provide remote, online access by patients to medical information, and by caregivers to up-to-date test results reflecting the health of patients.

The device can be used in the hospital, physician's office, clinic, and patient's home either by the patient or an attendant care giver. In one embodiment, the invention is practiced in the patient's home allowing the patient to be monitored, his or her therapy optimized, and adverse events that require hospitalization to be avoided.

The device can provide information on the patient's status and provide instructions or other actionable information to the healthcare professional and/or the patient. Examples, without limitation, of instructions that can be given include: change diuretic dose, withhold diuretic, introduce another diuretic, contact caregiver, no change in care plan necessary, change fluid intake, withhold potassium supplementation, and increase potassium supplementation. The objective is to track the patient's condition and steer him or her toward a stable condition through appropriate interventions made by the patient or the caregiver. Algorithms for treatment decisions are known. An example of a set of treatment algorithms can be found in: Healthcare Guideline; Congestive Heart Failure in Adults, Institute for Clinical Systems Improvement, Release July 2003; and Silver M, Pisano C, Cianci P, Outpatient management of heart failure: Program development and experience in clinical practice, Advocate Christ Medical Center, Oak Lawn, Ill., Post Graduate Institute for Medicine 2003, each of which is incorporated by reference in its entirety.

Decision Points

The device can be configured to respond to the measured level of a biomarker, in particular when the level of the biomarker indicates a change in the patient's health status. For example, the device can be configured to store the results of tests and determine changes in the levels of markers over time. A change in results over time can be an acute change or a chronic change. An acute change can be a significant change in the level of a biomarker over a short period of time. The magnitude of change and period of time can be different for each biomarker. The device can be configured to compare each new test result either to a stored values of recent test results (e.g., the previous 1, 2, 3, 4, 5 or more results), or to an aggregate measure of recent test results (such as an average) to determine if an acute change has occurred. In one example, an acute change is detected by the percentage change in a test result from the previous result.

Chronic changes can be detected as well. A chronic change can be a change in the level of a biomarker that occurs over a long period of time. For example, a chronic change can occur such that many testing intervals pass without an acute change being detected, yet the level of biomarker is significantly different. To detect a chronic change, the device can compare the results of each new test to a stored result of an earlier test, or to an aggregate measure of earlier tests. For detecting chronic changes, the earlier test can be, for example, 4-12 weeks prior to the new test result. In one example, the aggregate measure can be a rolling average, such as a 4-week, 8-week, or 12-week rolling average.

The device can also be configured to compare test results to a stored threshold value or range. The threshold value can be an upper or lower limit or range of values. Thus, the device can determine if the measured value of a marker, or group of markers, is a safe level, a dangerous level, or indicates an emergency. The device can alert the patient to the results of the test and can be configured, when appropriate to instruct the patient to seek medical care.

The device can also be configured to track combinations of markers, for example, an average value of two markers, the difference in level between two markers, a ratio of the levels of two markers, or whether two or more markers exceed their respective threshold values at the same time. The device can be configured to track one or more markers in combination with a patient's signs and symptoms.

The device can be personalized for a patient. The threshold values and other parameters for each biomarker can be adjusted (for example, by a physician or other caregiver) based on the circumstances of the patient, such as, for example, age, gender, or disease status. The questions and responses that the device presents to the patient can also be adjusted.

Examples of how the device can record, detect changes, and respond to detected changes in the level of a biomarker are presented below. The threshold values and levels of biomarkers referred to below are not limiting, may not be appropriate for all patients, and are for purposes of example only.

Marker of Left Ventricular Volume Overload and Myocardial Stretch

In one embodiment, the device is configured to measure the biomarker BNP in a patient sample. The device can track the patient's BNP level as a function of time and detect changes in the BNP level. The changes can be acute or chronic. When a change in BNP level is detected, the device can respond with a request for additional input for the patient or instructions for the patient.

The device can determine a patient's baseline level of BNP, against which future measurements of BNP will be compared. The baseline level can be set based on data on the influence of the patient's gender, age, body mass, and degree of hypertrophy. The baseline can also be refined to set reasonable treatment targets for a patient taking into consideration the degree of disease comorbidities and the patient's prognosis. A series of BNP measurements can be used to set a baseline for a patient.

For example, the baseline can be defined as the average of the most recent two test results with an increase of maximum 10% (compared to the previous baseline) out of the last four tests. The following test results are excluded from the calculation:

Any test result flagged with an acute symptom

Any test of the 2 used for the calculation is older than 28 days

The last 4 tests have been done in less than 4 days

Under certain conditions, no baseline value will be available, such as the first use of the device (i.e., no test results have been recorded); after the device has been reset; or when any of the test results used for the baseline calculation is older than 28 days. By testing 4 times over at least 4 days, the initial baseline can be calculated. When the baseline is defined in this way, the device cannot give warnings for acute deterioration over this initial 4 day period. In case one value of the two used for the calculation is older than 28 days, one additional test can be sufficient to calculate the baseline. The baseline can be a variable baseline, changing as the most recent test results change in value.

The device can detect acute changes in BNP level, and advise the patient to take appropriate responses. Criteria for determining an appropriate response can include the patient's initial BNP level, which can reflect the patient's risk profile; the percentage change in BNP level; the presence or absence of acute symptoms; and the evolution of BNP values to confirm a trend and exclude assay-to-assay, physiological, and statistical variations. When an acute increase in BNP level is detected by the device, the device can query the patient for the presence of acute symptoms. In advising a patient of a response to take to an increased BNP levels, the presence of one or more acute symptoms can be a deciding factor. Acute symptoms can include chest pain (AMI); a squeezing or crushing chest feel (AMI); pain radiating to neck, left arm (AMI); sweating, nausea, or vomiting (AMI, Stroke, pulmonary TE); loss of consciousness; acute dyspnea (AMI, decompensation, pulmonary thrombo-embolism); palpitations without exercise; dyspnea when laying down (right heart decompensation); sudden headache (stroke); and sudden vision impairment (stroke). See, for example, Harrisson T. R. et al, Principles of Internal Medicine. McGraw Hill, Inc. 1983, 1432-34 & 1353-58 & 2038-39, which is incorporated by reference in its entirety. When the patient indicates that any acute symptoms are present, the device can advise the patient to seek medical care at once.

If there is an acute increase in BNP level, but the patient is not experiencing any acute symptoms, the device's response can depend on the percentage change in BNP level and the absolute BNP level. In general, a large percentage increase in BNP level and a high absolute level can indicate a deterioration in the patient's condition, and the device can respond by prompting the patient to seek medical care at once. A smaller percentage change and lower absolute level may not require immediate medical attention, and the change in BNP level can be confirmed by a second test. In one example, the severity of a patient's disease can be stratified by absolute BNP levels as follows (see, for example, Clerico A, et al. *Clin Chem Lab Med* 2002 April;40(4): 371-7; and Nomura H, et al. *J Am Geriatr Soc* 2002 September;50(9): 1504-9, each of which is incorporated by reference in its entirety):

<20 pg/mL Healthy 20-50 pg/mL 1 risk factor: hypertension or age 50-100 pg/mL 2 risk factors: hypertension, age, post-AMI >100 pg/mL chronic hart failure patient NYHA classes 1-4

Changes in BNP level can also be grouped by severity, for example, no increase, an increase of less than 10%, 10-20%, 20-30%, 30-40%, or 40% or more.

A second test can exclude assay-to-assay or physiological variations and thus confirm the increase. The second test can be given after a predetermined interval, which can vary depending on the severity of the increase (e.g., within 30 minutes, 60 minutes, the same day, or within 24 hours of the first test). If the second test result is a lower BNP value, then a third test can be performed. The third test can confirm an increase in this case, or, for example, exclude a non-pathological transient rise of more than 20% due to exercise.

For example, if the BNP level increases by 10% or less (and the patient has no acute symptoms), the device can prompt the patient to perform a second test. The second test can be performed the next day (for example, if the patient's BNP level is less than 50 pg/mL) or sooner, such as thirty minutes later (for example, if the patient's BNP level is 50 pg/mL or greater). If the BNP level has increased by 10-20%, the device can prompt the patient to perform a second test, for example, within thirty minutes of the first test. If the BNP level has increased by more than 20%, the device can prompt the patient to seek medical care at once. An increase of more than 30% can be regarded as the strongly indicative for ischemia and AMI or an acute heart decompensation. See, for example, Kyriakides ZS, et al. *Clin Cardiol* 2000 April;23(4): 285-8; and Nakamura T, et al. *J. Am. Coll. Cardiol*. 2002 May 15;39 (10): 1657-63, each of which is incorporated by reference in its entirety. If the patient's BNP level has not increased, or increased by less than 5%, the device can prompt the patient to perform a second test at a predetermined interval, such as seven days.

The device can respond to the results of the second test. If the second test is performed on the day after the previous test (e.g., when the patient's BNP level is less than 50 pg/mL), the device can respond as follows. If the second test reveals a BNP level more than 20% above the baseline, the patient is instructed to seek medical care at once. The patient can be instructed to perform a third test if the second test reveals a BNP level that is between 0 and 20% higher than the baseline. The third test can be performed, for example, on the day following the second test. If the third test indicates that the patient's BNP level is between 10% and 20% higher than the baseline, the patient is instructed to seek medical care at once. However, if the third test reveals a BNP level between 0 and 10% higher than the baseline, the baseline can be adjusted to the average of the previous baseline and the result of the third test. The patient is instructed to resume a regular test schedule, such as once a week.

If the second test is performed within thirty minutes of the previous test (e.g., when the patient's BNP level is 50 pg/mL or greater), the device can respond as follows. When the second test result is 20% or more above the baseline, the patient is instructed to seek medical care at once. The patient can be instructed to perform a third test if the second test reveals a BNP level that is between 0 and 20% higher than the baseline. The third test can be performed within thirty minutes of the second test (such as when the second test result was between 10% and 20% above the baseline) or within four hours of the second test (such as when the second test result was between 0 and 10% above the baseline). If the third test indicates that the patient's BNP level is between 10% and 20% higher than the baseline, the is instructed to seek medical care at once. However, if the third test reveals a BNP level between 0 and 10% higher than the baseline, the baseline can be adjusted to the average of the previous baseline and the result of the third test. The patient is instructed to resume a regular test schedule, such as once a week.

Chronic Changes

The device can detect chronic changes in BNP level; in other words, slow changes that accumulate over time to reflect a change in the patient's condition. A chronic change can be measured, for example, by observing changes in a rolling average of BNP values, such as a rolling 2-week average. To exclude increases of an acute nature, or due to a temporary event (such as exercise), only those chronic increases that are manifested for at least two weeks where the increases outnumber the decreases can be considered as chronic increases. A chronic increase can be small (e.g., approximately 10%) when consistent over a long time (such as one month) or can be large (for example, approximately 20%) over a relatively short term (such as two weeks). It can be important to exclude increases due to assay-to-assay variability, physiological rises, etc., before concluding that a chronic increase has occurred. In order to due so, sufficient test results have to be available. Therefore, upon suspicion of a chronic increase, patients can be instructed to perform more tests.

A rolling average can be the average of test results performed within a given time frame. For example, a rolling two week average can be the average of results recorded over the previous 15 days, a rolling 4 week average can be the average of results recorded over the previous 29 days, and a rolling 12 week average can be the average of results recorded over the previous 85 days. When calculating a rolling average, any test result recorded with an acute symptom flag (i.e., a test result where the patient was suffering an acute symptom at the time of the test) can be excluded. Under certain circumstances, a rolling average cannot be calculated, such as the first use of the system, following a system reset, or when the system has not been used over the relevant length of time (e.g., 2, 4 or 12 weeks). By testing once a week over at least 15 days (three test results), an initial 2-week rolling average can be calculated. This means that the device cannot give warnings for chronic deterioration over this initial 2-week period.

When a chronic increase in BNP levels is detected, the device can query the patient for the presence of chronic symptoms. Examples of chronic symptoms include increasing fatigue in general (heart performance reduction); shortening of walking distance or step climbing (heart performance reduction); aggravating chronic dyspnea (right heart decompensation, multiple pulmonary thrombo-embolism); palpitations without exercise; aggravating dyspnea when laying down (decompensation); aggravating swollen feet or legs; or memory loss or paralysis or equilibrium disturbance. When the patient indicates that any chronic symptoms are present, the device can advise the patient to seek medical care at once.

If there is a chronic increase in BNP level, but the patient is not experiencing any chronic symptoms, the device's response can depend on the percentage change in BNP level and the absolute BNP level. In general, a large percentage increase in BNP level and a high absolute level can indicate a deterioration in the patient's condition, and the device can respond by prompting the patient to seek medical care at once. A smaller percentage change and lower absolute level may not require immediate medical attention, and the change in BNP level can be confirmed by a second test. In one example, the severity of a patient's disease can be stratified by absolute BNP levels as follows:

<20 pg/mL Healthy
20-50 pg/mL 1 risk factor: hypertension or age
50-100 pg/mL 2 risk factors: hypertension, age, post-AMI
>100 pg/mL chronic hart failure patient NYHA classes 1-4

Chronic changes in BNP level can also be grouped by the duration in the change, for example, a change in the two-week rolling average, a change in a 4-week rolling average, or a change over a longer interval, such as a change in the 12-week rolling average. In each of these time periods, the changes in BNP level can be grouped by severity, such as no increase, an increase of greater or less than 7.5%, an increase of greater or less than 15%, an increase of less than 10%, an increase of 10-30%, an increase of 30-50%, or an increase of more than 50%.

For example, when the device detects a small, chronic increase in the two-week rolling average (e.g., an increase of less than 10%) in the patient's BNP level, and the patient reports no chronic symptoms, the device can instruct the patient to perform a second test after a predetermined interval, such as 7 days. If there is a moderate increase in the patient's two-week rolling average BNP level (e.g., an increase of 10-30%), the device can instruct the patient to perform a second test after a predetermined interval, such as within 24 or 48 hours. A large increase (e.g., of 30-50%) and a small absolute BNP level (e.g., less than 50 pg/mL) can cause the device to instruct the patient to perform a second test after a predetermined interval, such as within 24 or 48 hours. When the device detects a severe increase (e.g., of more than 50%) in the two-week rolling average, it can instruct the patient to seek medical care at once.

If the second test result is a BNP level higher than the previous two-week rolling average, the device can instruct the patient to seek medical care at once. If, on the other hand, the second test result is lower than the previous result, the device can instruct the patient to perform additional test (e.g., one test each day) until the BNP level either returns to its previous level, or the BNP level increases, which will result in a prompt to the patient to seek medical care at once. If the BNP level does not return to its previous level or increase within one week, the device can prompt the patient to seek medical care at once.

When there is a small increase in the 4-week rolling average (e.g., an increase of less than 15%), and the patient reports no chronic symptoms, the device can instruct the patient to perform a second test after a predetermined interval, such as 7 days. When there is a large increase in the 4-week rolling average (e.g., an increase of 15% or greater), the device can instruct the patient to report to his or her health care provider.

When there is a small increase in the 12-week rolling average (e.g., an increase of less than 7.5%), and the patient reports no chronic symptoms, the device can instruct the patient to perform a second test after a predetermined interval, such as 7 days. When there is a large increase in the 4-week rolling average (e.g., an increase of 7.5% or greater), the device can instruct the patient to report to his or her health care provider.

The parameters used by the devices (i.e., the values of percentage change in BNP level, absolute BNP level, patient messages, etc.), can be altered. For example, a physician or other health care provider can adjust the value of acute increase in BNP level required to prompt the patient to seek medical care to a desired value. In this way, the behavior of the device can be tailored according to the preferences of a physician or to the needs of a particular patient or group of patients.

Markers of Renal Function

The following uses, by example, the biomarker creatinine. The accepted method for use in routine care is a measure of creatinine using adjustment with the Cockroft and Gault equation. Creatinine can provide important information on volume status and should be followed in patients during optimization of pharmacological agents (e.g. an ACE inhibitor) and ideally throughout the patient's care. Tests are performed by the patient or the healthcare provider every day, at a suitable testing interval, or with the onset of certain signs and symptoms. An increase in serum creatinine of 0.05 to 0.5 mg/dL is an indication for reassessment of volume status. Renal function declines with age; many elderly patients have a glomerular filtration rate below 50 mL/minute. Further, as stated, an early increase of <30% in the concentration of creatinine is expected when a patient is administered an ACE inhibitor. GFR monitoring using, for example, creatinine is important in these patients.

Further, when using BNP to guide the optimization of pharmacological treatment, an estimate of GFR is essential to avoid under-hydration. An 'action level' (e.g. a level that defines a significant reduction in renal perfusion) for GFR will require the healthcare professional and/or the patient to follow a predefined intervention dependent on the rate of change of GFR over time and the absolute level. An intervention might include a change in diuretic dose, withhold the diuretic, introduce another diuretic, change fluid intake, withhold potassium supplementation, increase potassium supplementation, contact the healthcare professional, refer to the Emergency Department, etc). As described, alternative markers of GFR can be used, such as Cystatin C.

Renal function can also be used as a prognostic marker, to provide information on a patient's health over a long period of time. The prognostic value of a measure of renal function (e.g., GFR as determined by a creatinine or Cystatin C measurement) can be independent of the use of renal function to monitor hydration on a short-term basis (e.g., during diuretic use). An average measure of renal function determined over a period of time can be used for prognostic purposes. See, for example, Koenig W, et al. *Clin Chem.* 10.1373/clinchem.2004.041889 2004 November; and Gottlieb S S, et al., *J Card Fail.* 2002 June;8(3):136-41, each of which is incorporated by reference in its entirety.

Marker of Myocardial Apoptosis or Injury

Measurement of a marker of myocardial apoptosis or injury, such as a troponin, in a remote setting using frequent testing is clinically useful. Tests are performed by the patient or the healthcare provider every day, at a suitable testing interval, or with the onset of certain signs and symptoms.

Marker of Inflammation

Measurement of a marker of inflammation in a remote setting is clinically useful. The marker of inflammation can include, for example, E-selectin, P-selectin, intracellular adhesion molecule-1, vascular cell adhesion molecule-1, Nourin-1, interleukin-1β, interleukin-6, interleukin-8, interleukin-10, tumor necrosis factor-alpha, hs-CRP, neutrophils, or white blood cell count. Tests are performed by the patient or the healthcare provider every day, at a suitable testing interval, or with the onset of certain signs and symptoms.

Marker of Anemia

Measurement of a marker of anemia, such as hemoglobin or hematocrit, in a remote setting using frequent testing is clinically useful. Tests are performed by the patient or the healthcare provider every day, at a suitable testing interval, or with the onset of certain signs and symptoms.

Markers of Myocardial Ischemia

Chronic myocardial ischemia is the leading cause of impaired myocardial contractility and heart failure. Ischemia markers (e.g. ischemia modified albumin, oxygen-regulated peptide, and free fatty acid) have a faster release profile than early necrosis markers (e.g. myoglobin or fatty acid binding protein (H-FABP)). Tests are performed by the patient or the healthcare provider every day, at a suitable testing interval, or with the onset of certain signs and symptoms.

Markers of Electrolyte Balance and Markers of Sodium Retention

Levels of electrolyte balance and sodium retention may be determined by measurement of the levels of sodium and potassium ion concentrations in serum. This may be conveniently done using ion selective electrodes.

EXAMPLES OF USE

The diagnostic kit can be used in a remote care setting (e.g. the patient's home, a nursing home, etc).

1. Optimization of Therapy 1.1 Normalize the Patient's Fluid Balance Using Diuretics.

BNP levels will fall as the patient's fluid balance is returned to normal. If adequate diuresis cannot be achieved with a single diuretic (e.g., a loop diuretic), a second diuretic will be necessary (e.g., a thiazide diuretic). Careful monitoring of renal function and electrolyte balance is necessary. BNP levels cannot be used as the sole marker of achieving a safe fluid balance.

1.2 Introduction of an ACE Inhibitor

ACE inhibitors improve prognosis mainly through their vasodilatory effect. Patients are at a high risk of renal dysfunction and hypotension—this has resulted in under-dosing and under-use.

Impaired renal function can be reversed by pulling back on the diuretic dose without needing to down-titrate the ACE inhibitor dose.

Monitoring renal function when up-titrating an ACE inhibitor will assure the physician that renal function is not compromised.

Doses should be up-titrated over 1-4 weeks to reach target doses. If adverse events occur which cannot be overcome by reducing the diuretic or holding at the current dose for longer, then alternative drugs should be used (e.g., angiotensin II receptor blocker (ARB) and/or hydralazine/isosorbide dinitrates).

Effective treatment will result in a gradual fall in BNP. Measurement of a GFR marker will identify reduced renal perfusion. Sudden increases in BNP will indicate volume overload.

1.3 Introduction of a Beta-Blocker

As stated, beta-blockers reduce the harmful effects of excessive and continuous increased adrenergic drive on the heart and lead to improvements in ventricular structure and function. There is an initial and transient decrease in contractility.

However, beta-blockers also reduce heart rate and blood pressure and therefore need careful introduction and up-titration. Up-titration of a beta-blocker should be delayed when volume overload is present.

The initial dose needs to be up-titrated every 2-4 weeks as tolerated. Patients must be monitored for hypotension, fluid retention, and bradychardia. If any of these persist, the dose should be lowered until tolerated and then increased again, more gradually.

Effective treatment will result in a gradual fall in BNP. Sudden increases in BNP will indicate volume overload.

2. Maintenance of Therapy

Assuming that target drug levels have been achieved, the patient would normally be responsible for tracking daily weight and be asked to comply with an appropriate diet. Some patients are allowed responsibility for their diuretics—for example, rapid weight gain can then be offset by up-titrating the diuretic dose for a day or so. The diagnostic would be used to:

i) detect the onset of decompensation
ii) steer diuretics/water/salt to maintain a 'normal fluid balance'
iii) provide the patient with a 'number' to reinforce well-being and promote compliance Changes in renal function caused by the introduction of an ACE inhibitor are tolerable and, in fact, an ACE inhibitor has a beneficial effect on the kidneys. It is agreed, however, that GFR still needs to be closely tracked to i) assess the impact of an ACE inhibitor on renal function and ii) to track for evidence of dehydration through over-use of diuretics.

A patient receiving a synthetic BNP (e.g., neseritide) as part of their treatment can be monitored. The synthetic BNP can be administered as an acute treatment (i.e., in response to an acute event) or a chronic treatment (i.e., to treat a chronic condition). In particular, the patient's inherent BNP production can be measured by measuring the patient's N-BNP (the inactive, N-terminal portion of proBNP). Synthetic BNPs do not include N-BNP. N-BNP is therefore a marker of the patient's BNP production, and is not affected by administration of a synthetic BNP.

3. Tracking Exercise Training

For some patients, exercise training improves cardiac health. However, the training regimen must be calibrated to avoid overexertion. The device can track the patient's training regimen, for example by recording the frequency and duration of exercise. The records can by the patient as a log, for example, with date, time, and a description of the exercise, or the device can be connected to an piece of exercise equipment such as a treadmill, and make recordings directly from the piece of equipment.

Tracking of exercise can be done in conjunction with measurement of actual heart function using biomarkers. For example, short- and long-term changes in a biomarker can provide information on how well the patient is responding to the exercise training.

The device can provide instructions or reminders to the patient to exercise, as well as query the patient with regards to signs and symptoms during and after exercise. For example, if a patient's symptoms worsen after exercise, the device can suggest a decrease in frequency or intensity of exercise, or alert a health care provider. If the patient's health is improving with exercise, the device can suggest an increase in frequency or intensity of exercise. A health care provider can obtain records of the patient's exercise from the device.

Other embodiments are within the scope of the following claims.

What is claimed is:

1. A method of monitoring a patient comprising:
    measuring in a sample taken from a patient, a level of a brain natriuretic peptide (BNP), and a level of a marker of renal function;
    recording multiple measurements of the level of BNP and the level of the marker of renal function;
    comparing a newly recorded level of BNP to the recorded measurements of the level of BNP;
    comparing a newly recorded level of the marker of renal function to the recorded measurements of the level of the marker of renal function; and
    determining if the changes in the level of BNP and marker of renal function are indicative of an acute or chronic change in the patient's heart condition based on the patient's gender, body mass, age or disease status.

2. The method of claim 1, further comprising measuring a weight, a heart rate, variability of heart rate, a breathing rate, a blood pressure, a temperature, a blood oxygen saturation, or an electrocardiogram of the patient.

3. The method of claim 1, wherein the marker of renal function includes creatinine or Cystatin C.

4. The method of claim 1, wherein BNP includes active BNP and an inactive BNP (N-BNP).

* * * * *